(12) United States Patent
Belk et al.

(10) Patent No.: US 9,872,728 B2
(45) Date of Patent: Jan. 23, 2018

(54) APPARATUSES AND METHODS FOR AFFIXING ELECTRODES TO AN INTRAVASCULAR BALLOON

(71) Applicant: St. Jude Medical, Cardiology Division, Inc., St. Paul, MN (US)

(72) Inventors: Paul A. Belk, Maple Grove, MN (US); Jennifer M. Heisel, Princeton, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 386 days.

(21) Appl. No.: 14/305,806

(22) Filed: Jun. 16, 2014

(65) Prior Publication Data

US 2015/0005762 A1 Jan. 1, 2015

Related U.S. Application Data

(60) Provisional application No. 61/840,807, filed on Jun. 28, 2013.

(51) Int. Cl.
*A61B 18/14* (2006.01)
*A61B 17/00* (2006.01)
(Continued)

(52) U.S. Cl.
CPC ........ *A61B 18/1492* (2013.01); *A61N 1/0551* (2013.01); *A61B 18/02* (2013.01);
(Continued)

(58) Field of Classification Search
CPC .. A61B 2018/00214; A61B 2018/0022; A61B 2018/00285
See application file for complete search history.

(56) References Cited

U.S. PATENT DOCUMENTS 3,650,277 A 3/1972 Sjostrand et al.
4,658,819 A 4/1987 Harris et al.
(Continued)

FOREIGN PATENT DOCUMENTS

WO 97/45157 12/1997
WO 00/66020 11/2000
(Continued)

OTHER PUBLICATIONS

Dibona, Gerald F., Renal Innervation and Denervation: Lessons from Renal Transplantation Reconsidered, Artificial Organs, vol. 11, No. 6, 1987, 457-462.
(Continued)

*Primary Examiner* — Jaymi Della
(74) *Attorney, Agent, or Firm* — Armstrong Teasdale LLP

(57) ABSTRACT

A catheter includes an inflation balloon and at least one electrode. The inflation balloon is inflatable within a vessel. The at least one electrode extends around at least a portion of a periphery of the inflation balloon. The at least one electrode is expandable as the inflation balloon is inflated, and contracts as the inflation balloon is deflated. The at least one electrode is held in place along a length of the inflation balloon with a tether member, which is secured at opposing distal and proximal ends of the inflation balloon.

12 Claims, 12 Drawing Sheets

(51) Int. Cl.
  *A61B 18/00* (2006.01)
  *A61N 1/05* (2006.01)
  *A61B 18/02* (2006.01)
  *A61B 18/18* (2006.01)
  *A61B 18/20* (2006.01)

(52) U.S. Cl.
  CPC .......... *A61B 18/1815* (2013.01); *A61B 18/20* (2013.01); *A61B 2017/00526* (2013.01); *A61B 2018/0022* (2013.01); *A61B 2018/00267* (2013.01); *A61B 2018/00285* (2013.01); *A61B 2018/00345* (2013.01); *A61B 2018/00404* (2013.01); *A61B 2018/00434* (2013.01); *A61B 2018/00511* (2013.01); *A61B 2018/00577* (2013.01); *A61B 2018/00839* (2013.01); *A61B 2018/1407* (2013.01); *A61B 2018/1475* (2013.01); *A61N 1/056* (2013.01); *A61N 1/0558* (2013.01)

(56) References Cited

U.S. PATENT DOCUMENTS

| | | | |
|---|---|---|---|
| 4,709,698 A * | 12/1987 | Johnston | A61B 18/08 604/114 |
| 5,035,694 A | 7/1991 | Kasprzyk et al. | |
| 5,255,679 A | 10/1993 | Imran | |
| 5,300,068 A | 4/1994 | Rosar et al. | |
| 5,311,866 A * | 5/1994 | Kagan | A61B 5/042 29/872 |
| 5,368,591 A | 11/1994 | Lennox et al. | |
| 5,387,233 A | 2/1995 | Alferness et al. | |
| 5,465,717 A | 11/1995 | Imran et al. | |
| 5,531,779 A | 7/1996 | Dahl et al. | |
| 5,598,848 A | 2/1997 | Swanson et al. | |
| 5,607,462 A | 3/1997 | Imran | |
| 5,628,313 A | 5/1997 | Webster, Jr. | |
| 5,676,662 A | 10/1997 | Fleischhacker et al. | |
| 5,707,400 A | 1/1998 | Terry, Jr. et al. | |
| 5,769,077 A | 6/1998 | Lindegren | |
| 5,772,590 A | 6/1998 | Webster, Jr. | |
| 5,893,885 A | 4/1999 | Webster, Jr. | |
| 5,897,553 A | 4/1999 | Muller et al. | |
| 5,954,649 A | 9/1999 | Chia et al. | |
| 5,954,719 A | 9/1999 | Chen et al. | |
| 6,004,269 A | 12/1999 | Crowley et al. | |
| 6,012,457 A | 1/2000 | Lesh | |
| 6,016,437 A | 1/2000 | Tu et al. | |
| 6,024,740 A | 2/2000 | Lesh et al. | |
| 6,073,048 A | 6/2000 | Kieval et al. | |
| 6,096,037 A | 8/2000 | Muller et al. | |
| 6,117,101 A | 9/2000 | Diederich et al. | |
| 6,135,997 A | 10/2000 | Laufer et al. | |
| 6,161,543 A | 12/2000 | Cox et al. | |
| 6,178,349 B1 | 1/2001 | Kieval | |
| 6,200,312 B1 | 3/2001 | Zikorus et al. | |
| 6,216,044 B1 | 4/2001 | Kordis | |
| 6,233,491 B1 | 5/2001 | Kordis et al. | |
| 6,283,951 B1 | 9/2001 | Flaherty et al. | |
| 6,287,608 B1 | 9/2001 | Levin et al. | |
| 6,292,695 B1 | 9/2001 | Webster, Jr. et al. | |
| 6,322,559 B1 | 11/2001 | Daulton et al. | |
| 6,460,545 B2 | 10/2002 | Kordis | |
| 6,522,926 B1 | 2/2003 | Kieval et al. | |
| 6,613,045 B1 | 9/2003 | Laufer et al. | |
| 6,616,624 B1 | 9/2003 | Kieval | |
| 6,635,054 B2 | 10/2003 | Fjield et al. | |
| 6,656,174 B1 | 12/2003 | Hedge et al. | |
| 6,669,655 B1 | 12/2003 | Acker et al. | |
| 6,699,231 B1 | 3/2004 | Sterman et al. | |
| 6,748,255 B2 | 6/2004 | Fuimaono et al. | |
| 6,805,131 B2 | 10/2004 | Kordis | |
| 6,845,267 B2 | 1/2005 | Harrison et al. | |
| 6,954,977 B2 | 10/2005 | Maguire et al. | |
| 6,970,730 B2 | 11/2005 | Fuimaono et al. | |
| 7,122,031 B2 | 10/2006 | Edwards et al. | |
| 7,149,574 B2 | 12/2006 | Yun et al. | |
| 7,155,284 B1 | 12/2006 | Whitehurst et al. | |
| 7,162,303 B2 | 1/2007 | Levin et al. | |
| 7,245,955 B2 | 7/2007 | Rashidi | |
| 7,291,146 B2 | 11/2007 | Steinke et al. | |
| 7,363,076 B2 | 4/2008 | Yun et al. | |
| 7,419,486 B2 | 9/2008 | Kampa | |
| 7,465,288 B2 | 12/2008 | Dudney et al. | |
| 7,468,062 B2 | 12/2008 | Oral et al. | |
| 7,481,803 B2 | 1/2009 | Kesten et al. | |
| 7,653,438 B2 | 1/2010 | Deem et al. | |
| 7,717,948 B2 | 5/2010 | Demarais et al. | |
| 7,742,795 B2 | 6/2010 | Stone et al. | |
| 7,850,685 B2 | 12/2010 | Kunis et al. | |
| 7,949,407 B2 | 5/2011 | Kaplan et al. | |
| 8,145,316 B2 | 3/2012 | Deem et al. | |
| 8,224,416 B2 | 7/2012 | de la Rama et al. | |
| 8,343,213 B2 | 1/2013 | Salahieh et al. | |
| 8,347,891 B2 | 1/2013 | Demarais et al. | |
| 8,442,639 B2 | 5/2013 | Walker et al. | |
| 8,454,594 B2 | 6/2013 | Demarais et al. | |
| 8,545,495 B2 | 10/2013 | Scheib | |
| 9,022,948 B2 | 5/2015 | Wang | |
| 2002/0068885 A1 | 6/2002 | Harhen et al. | |
| 2002/0120304 A1 | 8/2002 | Mest | |
| 2003/0050681 A1 | 3/2003 | Pianca et al. | |
| 2003/0060858 A1 | 3/2003 | Kieval et al. | |
| 2003/0074039 A1 | 4/2003 | Puskas | |
| 2003/0114739 A1 | 6/2003 | Fuimaono et al. | |
| 2003/0216792 A1 | 11/2003 | Levin et al. | |
| 2003/0233099 A1 | 12/2003 | Danaek et al. | |
| 2004/0215186 A1 | 10/2004 | Cornelius et al. | |
| 2005/0171525 A1 * | 8/2005 | Rioux | A61B 18/14 606/41 |
| 2005/0288730 A1 | 12/2005 | Deem | |
| 2006/0089678 A1 | 4/2006 | Shalev | |
| 2007/0135875 A1 | 6/2007 | Demarais et al. | |
| 2008/0255478 A1 | 10/2008 | Burdette | |
| 2009/0076409 A1 | 3/2009 | Wu et al. | |
| 2010/0016762 A1 | 1/2010 | Thapliyal et al. | |
| 2010/0094209 A1 | 4/2010 | Drasler et al. | |
| 2010/0121270 A1 * | 5/2010 | Gunday | A61B 17/22012 604/98.01 |
| 2010/0168737 A1 | 7/2010 | Grunewald | |
| 2010/0249773 A1 | 9/2010 | Clark et al. | |
| 2010/0268307 A1 | 10/2010 | Demarais et al. | |
| 2010/0286684 A1 | 11/2010 | Hata et al. | |
| 2011/0004087 A1 | 1/2011 | Fish et al. | |
| 2011/0118726 A1 | 5/2011 | de la Rama et al. | |
| 2011/0137298 A1 | 6/2011 | Nguyen et al. | |
| 2011/0160720 A1 | 6/2011 | Johnson | |
| 2011/0213231 A1 | 9/2011 | Hall et al. | |
| 2011/0257641 A1 | 10/2011 | Hastings et al. | |
| 2011/0264011 A1 | 10/2011 | Wu et al. | |
| 2011/0264086 A1 | 10/2011 | Ingle | |
| 2012/0143097 A1 | 6/2012 | Pike, Jr. | |
| 2012/0143298 A1 | 6/2012 | Just et al. | |
| 2012/0289982 A1 * | 11/2012 | Gunday | A61B 17/320725 606/159 |
| 2012/0296232 A1 | 11/2012 | Ng | |
| 2012/0323233 A1 | 12/2012 | Maguire et al. | |
| 2013/0116737 A1 | 5/2013 | Edwards et al. | |
| 2013/0131743 A1 | 5/2013 | Yamasaki et al. | |
| 2013/0144251 A1 | 6/2013 | Sobotka | |
| 2013/0172715 A1 | 7/2013 | Just et al. | |

FOREIGN PATENT DOCUMENTS

| | | |
|---|---|---|
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |
| WO | 2012009486 A2 | 1/2012 |

(56) References Cited

FOREIGN PATENT DOCUMENTS

| WO | 2012/064818 | | 5/2012 |
|---|---|---|---|
| WO | 2012/106492 | | 8/2012 |
| WO | 2013147335 | A1 | 10/2013 |

OTHER PUBLICATIONS

Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of The American Heart Association, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of The American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of The American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:I-13 (1982).
Grassi, Guido et al, Baroreflex Control of Sympathetic Nerve Activity in Essential and Secondary Hypertension, Hypertension Journal of The American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May 1994;266(5 Pt 2):F738-F745.
Hoobler, S.W. et al, The Effects of Splanchnicectomy on the Blood Pressure in Hypertension, Circulation Journal of The American Heart Association, vol. IV, Aug. 1951, 173-183.
Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6 (4):270-6.
Howard, James P. et al, Size of Blood Pressure Reduction from Renal Denervation: Insights from Meta-Analysis of Antihypertensive Drug Trials of 4121 Patients with Focus on Trial Design: the Converge Report, Heart 2013;0:1-9.
Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.
Howell, Marcus H. et al, Tandem Stenting of Crossed Renal Arteries with Ostial Stenosis, Tex Heart Inst J. 2000; 27(2): 166-169.
Hoye, Neil A. et al, Endovascular Renal Denervation: A Novel Sympatholytic with Relevance to Chronic Kidney Disease, Clinical Kidney Journal Advance Access, (2013) 0: 1-8.
Huang, Shod K. Stephen et al, Radiofrequency Catheter Ablation of Cardiac Arrhythmias, Basic Concepts and Clinical Applications, Wiley-Blackwell, Jun. 2000, 1-12.
Huang, Wann-Chu, Renal Denervation Prevents and Reverses Hyperinsulinemia-Induced Hypertension in Rats, Hypertension Journal of The American Heart Association, 1998;32:249-254.

(56) References Cited

OTHER PUBLICATIONS

Humpreys, Michael H., Renal Nerves and CKD: Is Renal Denervation the Answer?, Journal of the American Socity of Nephrology, 2012, 23: 1-3.
International Search Report and Written Opinion for Application No. PCT/US2010/054637 dated Jan. 3, 2011.
International Search Report and Written Opinion for Application No. PCT/US2010/054684 dated Jan. 10, 2011.
Irigoyen, M.C.C. et al, Baroreflex Control of Sympathetic Activity in Experimental Hypertension, Brazilian Journal of Medical and Biological Research, (1998) 31: 1213-1220.
Izzo, Jr, Joseph L. et al, The Sympathetic Nervous System and Baroreflexes in Hypertension and Hypotension, Current Hypertension Reports 1999, 3:254-263.
Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.
Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.
Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.
Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19/26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339 (2013).
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the Symplicity HTN-3 Trial, Clin. Cardiol. 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Kirchheim, H. et al, Sympathetic Modulation of Renal Hemodynamics, Renin Release and Sodium Excretion, Klin Wochenschr (1989) 67: 858-864.
Klein, GE et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.
Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.
Krum, Henry et al, Device-Based Antihypertensive Therapy: Therapeutic Modulation of the Autonomic Nervous System, Circulation. 2011;123:209-215.
La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.
Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.
Lambert, Gavin W. et al, Health-Related Quality of Life After Renal Denervation in Patients With Treatment-Resistant Hypertension, Hypertension. 2012;60:1479-1484.
Lee, Sang Joon et al, Ultrasonic Energy in Endoscopic Surgery, Yonsei Medical Journal, vol. 40, No. 6, pp. 545-549, 1999.
Leertouwer, Trude C. et al, In-Vitro Validation, with Histology, of Intravascular Ultrasound in Renal Arteries, Journal of Hypertension 1999, vol. 17 No. 2, 271-277.
Leishman, A.W.D., Hypertension—Treated and Untreated, British Medical Journal, May 1959, 1361-1368.
Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.
Levin, Stephen, Ardian: Succeeding Where Drugs Fail Treating Hypertension in the Cath Lab, In Vivo: The Business & Medicine Report, vol. 27, No. 10, Nov. 2009.
Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.
Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.
Luscher, Thomas F. et al, Renal Nerve Ablation After Symplicity HTN-3: Confused at the Higher Level?; European Heart Journal, doi:10.1093/eurheartj/ehu195; May 14, 2014.

(56) References Cited

OTHER PUBLICATIONS

Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.
Mahfoud, Felix et al, Expert Consensus Document from the European Society of Cardiology on Catheter-Based Renal Denervation, European Heart Journal, Jul. 2013;34(28):2149-57.
Mancia, Giuseppe et al, Sympathetic Activation in the Pathogenesis of Hypertension and Progression of Organ Damage, Hypertension Journal of The American Heart Association, 1999, 34:724-728.
McGahan, John P. et al, History of Ablation, Tumor Ablation, 2005, pp. 3-16.
Medtronic, Inc., J.P. Morgan Healthcare Conference, Corrected Transcript, Jan. 13, 2014, Factset:Callstreet, www.callstreet.com.
Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.
Medtronic, Inc., RDN Therapy with the Symplicity Renal Denervation System, Procedure Fact Sheet, www.medtronic.com, 2011.
Medtronic, Inc., Renal Denervation (RDN) Novel Catheter-based Treatment for Hypertension, Symplicity RDN System Common Q&A, 2011.
Medtronic, Inc., Scientific Basis Behind Renal Denervation for the Control of Hypertension, Dec. 2012, http://www.icimeeting.com/2012/images/stories/PDF/1448_Wilcox_I_Mon.pdf.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Meredith, I T et al, Exercise Training Lowers Resting Renal But Not Cardiac Sympathetic Activity in Humans; Hypertension Journal of The American Heart Association, 1991;18:575-582.
Michaelis, Lawrence L. et al, Effects of Renal Denervation and Renin Depletion on the Renal Responses to Intravascular Volume Expansion, Ann Surg. Mar. 1972; 175(3): 424-430.
Millard, F.C. et al, Renal Embolization for Ablation of Function in Renal Failure and Hypertension, Postgraduate Medical Journal (1989) 65, 729-734.
Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.
Mogil, Robert A. et al, Renal Innervation and Renin Activity in Salt Metabolism and Hypertension, American Journal of Physiology, vol. 216, No. 4, Apr. 1969, 693-697.
Morita, Hironobu et al, Neural Control of Urinary Sodium Excretion During Hypertonic NaC1 Load in Conscious Rabbits: Role of Renal and Hepatic Nerves and Baroreceptors, Journal of the Autonomic Nervous System, 34 (1991) 157-170.
Morrissey, D.M. et al, Sympathectomy in the Treatment of Hypertension, The Lancet, Feb. 1953, 403-408.
Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.
Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of The American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5 , pp. 253-255.
Oral, Hakan et al, Pulmonary Vein Isolation for Paroxysmal and Persistent Atrial Fibrillation, Circulation Journal of The American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., the Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, TIME Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.
Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14(4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.

(56) References Cited

OTHER PUBLICATIONS

Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of The American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, Jan. 10-15, 2002.
Pearce, John A. et al, Blood Vessel Architectural Features and Their Effect on Thermal Phenomena, Critical Reviews, vol. CR75, Bellingham, WA: SPIE Optical Engineering Press; 2000, p. 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3): 139-142.
Persu, Alexandre et al, Renal Denervation: Ultima Ratio or Standard in Treatment-Resistant Hypertension, Hypertension Journal of The American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.
Plouin, Pierre-Francois et al, Blood Pressure Outcome of Angioplasty in Atherosclerotic Renal Artery Stenosis A Randomized Trial, Hypertension Journal of The American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System an Overview of Structure and Function, Journal of Pharmacological and Toxicological Methods 44 (2000) 333-340.
Putney, John Paul, Are Secondary Considerations Still "Secondary"?: An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4: 1886-1891, 2009.
Zazgornik, Jan et al, Bilateral Nephrectomy: The Best, but Often Overlooked, Treatment for Refractory Hypertension in Hemodialysis Patients, AJH 1998; 11:1364-1370.
Abboud, Francois M., The Sympathetic System in Hypertension, State-of-the-Art Review, Hypertension Journal of the American Heart Association, Hypertension 4 (suppl II): II-208-II-225, 1982.
Allen, Edgar V., Sympathectomy for Essential Hypertension, Circulation Journal of the American Heart Association, vol. VI, Jul. 1952, 131-140.
Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.

Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6 (2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of The American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.

(56) References Cited

OTHER PUBLICATIONS

Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1):14-8.
Chabanier, H. et al, On the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review—Part II, Journal of the National Medical Association, May 1948, vol. 40, No. 3., 113-116.
Dailey, U.G., Surgical Treatment of Hypertension: A Review—Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension A Systematic Review and Meta-Analysis, Journal of the American College of Cardiology, vol. 62, No. 3, 2013, 231-241.
De Wardener, H.E., The Hypothalamus and Hypertension, Physiological Reviews,vol. 81, No. 4, Oct. 2001.
Dequattro V. et al, The Sympathetic Nervous System: The Muse of Primary Hypertension, Journal of Human Hypertension, 2002, 16 (Suppl 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F., Neural Control of Renal Function: Cardiovascular Implications, Hypertension Journal of The American Heart Association, vol. 13, No. 6, Part 1, Jun. 1989, 539-548.
Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of The American Heart Association, vol. 41, Mar. 2003, Part II, 621-624.
European Search Report for European Application No. 14174346, dated Nov. 26, 2014 (7 pp.).
Robbins, Ivan M. et al, Pulmonary Vein Stenosis After Catheter Ablation of Atrial Fibrillation, Circulation Journal of The American Heart Association, 1998;98:1769-1775.
Rocha-Singh, Krishna J., Catheter-Based Sympathetic Renal Denervation A Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4):94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of The American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of The American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, the Journal of The American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of The American Heart Association, 2001;37:1053-1059.

(56) References Cited

OTHER PUBLICATIONS

Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: an Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of The American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.
Teo, W S et al, Radiofrequency Catheter Ablation of Accessory Pathways: The Initial Experience in Singapore, Singapore Medical Journal, 1994; vol. 35:36-40.
Thiebot, J. et al, Bilateral Nephrectomy by Embolization of the Renal Arteries: A Report on Five Cases (author's transl), Sem Hop. Apr. 8-15, 1980;56(13-14):670-5.
Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of The American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Vonend, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.
Webb, R.L. et al, Functional Identification of the Central Projections of Afferent Renal Nerves, Clin. and Exper.—Theory and Practice, Ag(Suppl.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of The American Heart Association, 1989;13:870-877.
Young, Robert R. et al, Reversible Block of Nerve Conduction by Ultrasound Ultrasonic Blocking of Nerve Fibers, Arch Neurol. 1961;4(1):83-89.

\* cited by examiner

APPARATUSES AND METHODS FOR AFFIXING ELECTRODES TO AN INTRAVASCULAR BALLOON

RELATED APPLICATION

This application claims the benefit of U.S. Provisional Application No. 61/840,807, filed on 28 Jun. 2013, which is hereby incorporated by reference herein in its entirety.

TECHNICAL FIELD

The present disclosure relates generally to catheters, and more particularly, to apparatuses and methods for affixing electrodes to a balloon of a balloon catheter.

BACKGROUND

Renal denervation is a method whereby nerve activity involving the targeted kidney is blocked or suppressed. Excessive sympathetic nerve activity has been implicated in vasoconstriction, reduction in renal blood flow, retention of fluid and salt, elevated renin generation, over-activation of the renin-angiotension-aldosterone mechanism, increased catecholamine production and, ultimately, arterial hypertension. Thus, renal denervation is used to alter neural signaling mechanisms involving the kidney to treat hypertension and other related disorders.

Renal denervation is achieved through destruction of afferent and efferent nerve fibers that run adjacent to the renal arteries. Successful renal denervation results in lower systemic arterial blood pressure in a treated patient. Renal denervation has also been shown to have benefits in conjunction with current guideline-based treatment strategies in heart failure, diabetes, obesity, sleep apnea, and ventricular tachycardia (VT). A conventional renal denervation procedure involves introducing a radio-frequency (RF) ablation catheter, which ablates renal nerves at various locations using variable energy. Ideally, the operator's objective is to ablate as minimally as necessary to achieve an appropriate degree of renal denervation for the least amount of time and at the fewest locations.

SUMMARY

One aspect of the present disclosure relates to a catheter, which includes an inflation balloon and at least one electrode. The inflation balloon is inflatable within a vessel. The at least one electrode extends around at least a portion of a periphery of the inflation balloon. The at least one electrode is expandable as the inflation balloon is inflated. The at least one electrode is configured to provide at least one of ablation, electrical stimulation, and electrical sensing.

The catheter may include a non-conductive filament connected to the inflation balloon and to the at least one electrode to maintain a position of the electrode relative to the inflation balloon. The non-conductive filament may be connected to distal and proximal ends of the inflation balloon. The non-conductive filament may be connected to the distal and proximal end portions of the inflation balloon with one of a loop formed in the non-conductive filament and a bonding agent. The at least one electrode may include first and second electrodes positioned at spaced apart locations along a length of the inflation balloon. The catheter may include an elastic member coupled to the at least one electrode, wherein the elastic member provides a radially-inward force to the at least one electrode.

The at least one electrode may include a plurality of conductive links. The catheter may include at least one conductive filament coupled to at least some of the plurality of conductive links. The inflation balloon may be operable within the vessel between a deflated position and an inflated position, wherein the inflation balloon in the inflated position temporarily blocks blood flow through the vessel and positions the at least one electrode in contact with an inner surface of the vessel. The first electrode may be configured to electrically stimulate at least one nerve, and the second electrode may be configured to detect an electrical activity in the at least one nerve. The at least one electrode may be configured to ablate at least one of the vessel and a nerve associated with the vessel. The at least one electrode may include a plurality of conductive filaments.

Another aspect of the present disclosure relates to a catheter, which includes an inflation balloon and at least one electrode. The inflation balloon may be inflatable within a vessel. The at least one electrode may extend around at least a portion of a periphery of the inflation balloon. The at least one electrode may include a plurality of conductive links. A conductive filament may be connected to at least some of the plurality of conductive links.

The conductive filament may have a continuous loop construction. The plurality of conductive links may form a continuous loop structure. The at least one electrode may be expandable from a collapsed position during delivery to the vessel and an expanded position into contact with the vessel when the balloon is inflated. The catheter may include a controller and an electrical lead, wherein the electrical lead is coupled between the at least one electrode and the controller.

A further aspect of the present disclosure relates to a method of assembling an ablation catheter. The method includes providing a balloon catheter and at least one electrode, wherein the balloon catheter includes an inflation balloon, and the at least one electrode has a loop construction and is expandable from a collapsed position to an expanded position. The method further includes positioning the at least one electrode around at least a portion of a periphery of the inflation balloon, and tethering the at least one electrode to distal and proximal end portions of the inflation balloon to maintain an axial position of the at least one electrode along a length of the inflation balloon.

Tethering the at least one electrode may include connecting at least one non-conductive filament to the at least one electrode and to the distal and proximal end portions of the inflation balloon. The at least one electrode may include a plurality of conductive links coupled together, and the method may include connecting a conductive filament to at least some of the conductive links. The at least one electrode may include at least first and second electrodes, and tethering the at least one electrode may include holding the first and second electrodes at spaced apart locations along the length of the inflation balloon.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

Throughout the drawings, identical reference numbers designate similar, but not necessarily identical, elements.

DETAILED DESCRIPTION

Figure 1:
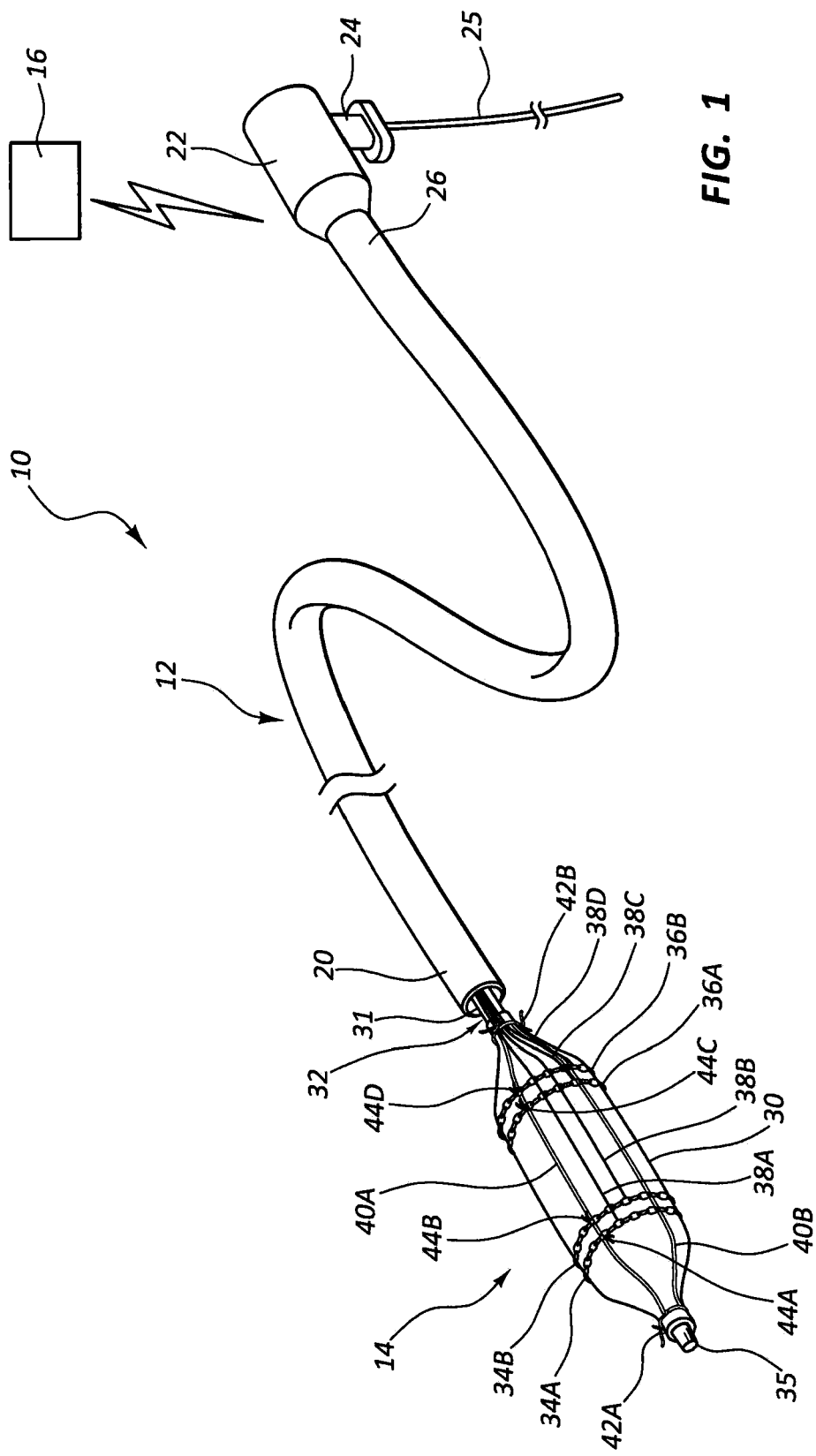
FIG. 1 is a perspective view of an example catheter in an inflated position in accordance with the present disclosure.

The apparatuses and methods disclosed herein are generally related to catheters, and more particularly related to ablation catheters for use in, for example, renal denervation procedures. A renal denervation procedure may include electrical stimulation of the renal artery as well as ablation of the renal artery. An ablation catheter may be used to perform at least one of the stimulating and ablating functions as part of the renal denervation procedure. The ablation catheter may be used to sense electrical activity in the renal artery and/or renal nerves associated with the renal artery. The ablation catheter may include a plurality of electrodes. At least some of the electrodes may operate to provide the stimulating and sensing functions, and some of the electrodes may operate to provide the ablation function. As discussed in further detail below, some of the electrodes may be capable of stimulating, sensing and ablating functions, while other electrodes may perform only some of the stimulation, sensing and ablation functions.

One aspect of the present disclosure relates to apparatuses and methods used to affix one or more electrodes to an inflation balloon of an ablation catheter. The electrodes may be affixed to the balloon in a way that permits expansion and contraction of the balloon within the renal artery while maintaining an axial position of the electrodes relative to the balloon.

The general structure and function of catheters used for ablating tissue in an artery (also referred to as ablation catheters) are known. The principles disclosed herein may be useful in conjunction with various catheters and methods of conducting denervation procedures. The catheter denervation devices and methods disclosed herein utilize an inflation balloon, which is operable within an artery to temporarily stop blood flow without causing adverse hemodynamic effects. The inflation balloon may also carry one or more electrodes used for ablating, electrically stimulating tissue near the artery, and/or sensing electrical activity in the artery or nerves associated with the artery. The inflation balloon, when inflated, may position the electrodes in contact with an inner surface of the artery. The inflation balloon may be an independent unit insertable into the artery. Alternatively, the inflation balloon may be embedded in the body of the ablation catheter or in the body of a delivery catheter for the procedure.

A successful ablation typically reduces nerve activity in the renal artery downstream of the ablation site (e.g., distally toward the kidney). The reduction in nerve activity, which typically corresponds to some functions of the kidneys, may include a permanent elimination of the nerve activity, a temporary reduction of the nerve activity, or simply a reduction in sympathetic vascular tone in the renal artery. The reduction in nerve activity in the renal artery may decrease blood pressure for the patient.

One procedure for denervation includes introducing a radio frequency ablation catheter into a renal artery and ablating nerves at several locations using variable energy up to, for example, about 8 Watts, in order to interrupt signaling between the central nervous system and the kidneys. The catheters of the present disclosure may provide a system for detecting that signaling, which can then be used to determine if the therapy is successful in interrupting the signaling.

In the present apparatuses, an electrode positioned around at least a portion of a periphery of an inflation balloon may be energized briefly in order to stimulate signal propagation with that part of the central nervous system that is associated with the kidneys. A separate electrode positioned around at least a portion of the periphery of an inflation balloon may be used to detect the signal propagation. The same or different electrodes positioned around at least a portion of the periphery of an inflation balloon may be operated to ablate the artery and associated nerves, followed by further stimulation and detecting with the electrodes.

In one embodiment, the electrodes may be assembled around an inflation balloon so that the electrodes are able to operate (e.g., conduct electricity) before, during, and/or after deployment of the inflation balloon. In other embodiments, the electrodes are positioned internal to the balloon or are integrated into portions of the balloon (e.g., between layers of the balloon or embedded in a sidewall of the balloon). The inflation balloon may include, for example, a polymer construction (e.g., thermoplastic or thermoset polymer resin such as polyethylene terephthalate (PET)). Many types of balloons, as known by those of skill in the art, may be used with the electrodes and electrode attachment features disclosed herein. The balloons may have any desired shape and size depending on, for example, the anatomy of the patient (e.g., the size and shape of the renal artery), the area of the patient being treated, and the type of electrode used for ablation and/or sensing.

The electrodes may have a continuous conductive filament construction. Alternatively, the electrodes may have a chain construction, which includes a plurality of individual rings, and may be referred to as chain electrodes. A chain electrode may include multiple linked rings of conductive material (e.g., silver and/or copper, etc.), which form a continuous loop. The electrode may have a fixed maximum diameter. For example, the chain electrode may be expandable from a reduced diameter configuration when the balloon is deflated or only partially inflated, to any diameter size up to the fixed maximum diameter depending on the inflated state and/or size of the inflation balloon.

Alternative embodiments for the electrodes may include electrodes that extend around only a portion of the perimeter of the balloon and have less than continuous circumferential construction. In other embodiments, only portions of a circumferential electrode may comprise conductive material or otherwise have the capability of stimulating, sensing or ablating. For example, only some of the rings of a chain electrode may include conductive material and be operable to stimulate, sense or ablate. The conductive portions of the electrode may be spaced apart around the balloon. In another embodiment, different portions of the electrode along its length may be operable at separate times.

In one configuration, at least one continuous filament or strand of wire may be threaded through one or more of the electrode links to provide improved conductivity between successive links. The at least one continuous filament or strand of wire may replace the chain electrode. The electrode may have a fixed maximum diameter, which may substantially correspond to an inflated diameter of the balloon. The electrode may be expandable and retractable between a small diameter configuration when the balloon is deflated and a large diameter configuration when the balloon is inflated to its intended maximum size. The electrode may comprise elastic materials and automatically retract from the large diameter configuration to the small diameter configuration upon deflation of the balloon. Other types of electrodes such as wires or elastic members having conductive properties may extend around at least a portion of a periphery of the inflation balloon to provide electrical conductivity, which may be continuous or discontinuous.

In some embodiments, an elastic filament may be threaded through one or more of the electrode links to apply a radially-inward-directed force that constricts the electrode against an outer surface of the inflation balloon. The elastic filament may hold the electrode in a plane arranged perpendicular to the longitudinal axis of the inflation balloon before, during and/or after inflation of the balloon.

Each electrode (e.g., conductive ring of a chain electrode) may be held circumferentially, or peripherally, around at least a portion of a balloon using a suitable type of longitudinal fastening affixed to the distal and proximal portions of the inflation balloon. The longitudinal fastening may include a plurality of tether members, each of which are connected to opposing distal and proximal ends of the inflation balloon, as well as being connected to each electrode. The tether members may be spaced apart around a periphery of the inflation balloon. A plurality of tether members may be used to hold each electrode in a predetermined orientation relative to the inflation balloon. The tether members may help maintain specific orientations of the electrodes relative to the balloon prior to and after inflation of the balloon.

The principles disclosed herein may be applicable to other apparatuses and methods used for treating other areas of the body, including, for example, any portion of the gastrointestinal, cardiovascular, nervous, hormonal, respiratory, excretory and reproductive systems of the body.

Figure 2:
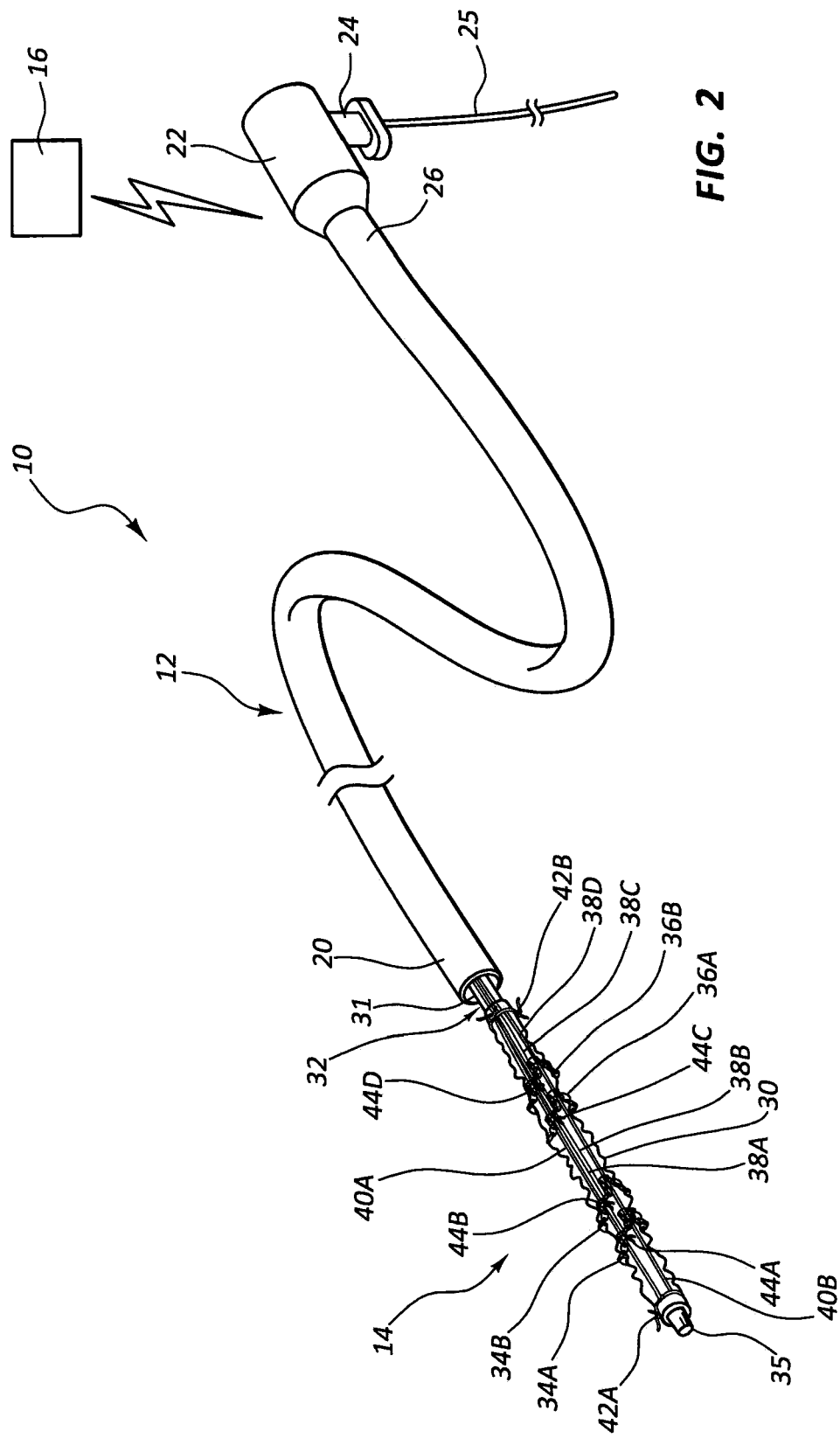
FIG. 2 is a perspective view of the catheter of FIG. 1 in a deflated position.

Referring now to FIGS. 1-2, an example catheter 10 is shown including an insertion tube 12, an inflation balloon assembly 14, a controller 16, and a hub 22. The insertion tube 12 includes distal and proximal ends 20, 26. The hub 22 includes an inlet port 24, which may be arranged in flow communication with the inflation balloon assembly 14 and a source of inflation fluid 25. The inflation balloon assembly 14 is positioned at the distal end 20 of the insertion tube 12.

Referring to FIGS. 1-3A, the inflation balloon assembly 14 may include an inflation balloon 30, an inflation tube 32, distal and proximal electrodes 34A-B, 36A-B, and electrode leads 38A-D. The inflation tube 32 may include proximal and distal ends 31, 35 and an inflation lumen 33 (see FIG. 3A). The inflation lumen 33 may be coupled in flow communication with the inlet port 24 of hub 22. The inflation balloon assembly 14 may also include a plurality of non-conductive filaments 40A-D (see FIG. 3A), distal and proximal filament anchors 42A-B (see FIG. 3), and electrode anchors 44A-D (see FIGS. 1 and 2) associated with each non-conductive filament 40A-D. The inflation balloon 30 may be replaceable with other types of balloons such as mechanically operated balloons.

The controller 16 (see FIGS. 1 and 2) may communicate with various features of the catheter 10 such as, for example, the electrodes 34A-B, 36A-B. The controller 16 may be electrically coupled to the electrodes 34A-B, 36A-B and other features (e.g., via the electrode leads 38A-D). The controller 16 may control, for example, the amount of energy delivered to the electrodes 34A-B, 36A-B, the on/off state of the electrodes 34A-B, 36A-B, and data collection provided by the electrodes 34A-B, 36A-B (e.g., a temperature reading or a signal level). As discussed further below, the electrodes 34A-B, 36A-B may operate, in response to signals from controller 16, to stimulate or ablate the renal artery, and/or sense activity in the renal artery and associated nerves.

The hub 22 is positioned at a proximal end 26 of the insertion tube 12. The hub 22 may include a pass-through opening which is connected in fluid communication with a lumen of the insertion tube 12. The insertion tube 12 includes distal and proximal ends 20, 26, and an internal lumen through which the inflation balloon assembly 14 is positioned during delivery of catheter to the renal artery (e.g., see renal artery 52 in FIG. 8). The inflation balloon assembly 14 may be deployed and positioned through the lumen of the insertion tube 12 a variable distance beyond the distal end of the insertion tube 12. With the inflation balloon 30 positioned distal of the insertion tube 12, as depicted in FIGS. 1 and 2, the inflation balloon 30 may be inflated to a predetermined pressure and/or predetermined size (e.g., diameter) to position the electrodes 34A-B, 36A-B in contact with an inner surface of the artery. In some configurations, a certain level of inflation pressure (i.e., a pressure measured within the inflation balloon 30 or at the source of inflation fluid 25) may be correlated to a certain inflated size of the inflation balloon 30.

The electrodes 34A-B, 36A-B are spaced apart along a length of inflation balloon 30. Any one of the electrodes 34A-B, 36A-B may be used to stimulate, ablate, and/or sense activity in the renal artery and associated nerves. In one arrangement, two of the electrodes 34A-B, 36A-B are used to ablate and two are used to stimulate and/or sense. The ablating electrodes may include one of the distal electrodes 34A-B and one of the proximal electrodes 36A-B. Alternatively, both distal electrodes 34A-B are ablating electrodes and both proximal electrodes 36A-B are stimulating and/or sensing electrodes, or vice versa. In another arrangement, all of the electrodes 34A-B, 36A-B are used to ablate or all are used to stimulate and/or sense.

Different numbers of electrodes 34A-B, 36A-B may be used in any given embodiment. For example, at least one distal electrode 34A-B, at least one proximal electrode 36A-B, or at least one of each of the distal and proximal electrodes 34A-B, 36A-B may be used with a single inflation balloon 30. Further, any of the various types of electrodes disclosed herein may be used alone or in combination with other numbers or types of electrodes for stimulating and/or ablating the renal artery or other area of a patient, or sensing activity in the renal artery or other area of the patient.

Using a pair of axially spaced apart electrodes (e.g., any two of electrodes 34A-B, 36A-B) may have advantages for at least the stimulating and/or sensing functions discussed herein. At least one upstream position (e.g., proximally away from the kidney) one of the electrodes 34A-B, 36A-B may operate to stimulate the renal artery and associated tissue (e.g., a renal nerve in the area of the renal artery). A separate one or more of the electrodes 34A-B, 36A-B positioned downstream of the upstream electrode (e.g., distally toward the kidney) senses changes in electrical activity in the renal artery and associated tissue. The sensed activity may be used in association with a renal denervation procedure.

The electrodes 34A-B, 36A-B may be positioned peripherally around at least a portion of an outer periphery of the inflation balloon 30, as depicted in FIGS. 1 and 2. In some embodiments, at least some of electrodes 34A-B, 36A-B extend around only a portion of the periphery of the inflation balloon 30. Alternatively, the electrodes 34A-B, 36A-B extend completely around the inflation balloon 30, but only portions thereof are conductive or operative for the purpose of stimulating, sensing and/or ablating the renal artery.

The electrodes 34A-B, 36A-B may be positioned at spaced apart locations along a length of the inflation balloon 30. The electrodes 34A-B may be referred to as distal electrodes and the electrodes 36A-B may be referred to as proximal electrodes. The electrodes 34A-B, 36A-B may be spaced apart axially along the length of the catheter 10 when the inflation balloon 30 is in an inflated state or a deflated state. Different numbers of electrodes may be used in other embodiments.

The electrodes 34A-B, 36A-B may include radiofrequency (RF) electrodes. In other embodiments, the electrodes 34A-B, 36A-B may include other types of energy sources such as, for example, ultrasound, laser, cryothermal, or microwave energy sources. The electrodes 34A-B, 36A-B may include, for example and without limitation, a continuous electrode comprising multiple linked rings 45 of conductive material to form an electrode chain. The chain construction of the electrodes 34A-B, 36A-B may permit expansion as the inflation balloon 30 is inflated, and retraction as the inflation balloon 30 is deflated.

The electrodes 34A-B, 36A-B may be dimensioned to permit the inflation balloon 30 to inflate to a full functional diameter within the renal artery without being constricted by the electrodes 34A-B, 36A-B to achieve contact of the electrodes 34A-B, 36A-B with the artery wall. A total circumferential length of the chain usually is slightly greater than an inner circumference of the artery wall. For example, an electrode 34A-B, 36A-B to be used inside an 8 mm internal diameter renal artery would have a circumferential length of about 26 mm, which is slightly greater than the internal diameter of the artery.

The size of each individual chain link 45 may be relatively small in comparison to the diameter of the artery. For example, each link 45 may have a length L (see FIG. 3A) in the range of about 1 mm to about 4 mm, and more particularly about 1.5 mm to about 2 mm. Links 45 may have a width W (see FIG. 3A) in the range of about 1 mm to about 2 mm, and more particularly about 1.1 mm to about 1.5 mm. Links 45 may have a diameter D (also referred to as a thickness—see FIG. 3A) in the range of about 0.1 mm to about 0.3 mm, and more particularly about 0.2 mm. The geometry of an individual chain link 45 is typically designed to maintain linearity among the electrodes 34A-B, 36A-B for wall apposition and to maintain compliance of electrodes 34A-B, 36A-B (e.g., avoid kinking and binding when links 45 move relative to each other) in both the fully expanded (deployed) and contracted (delivered) configurations of inflation balloon 30.

The materials used for the electrodes 34A-B, 36A-B (and all other conductive materials disclosed herein) may be bioelectrically compatible. Some example materials for electrodes 34A-B, 36A-B include silver, silver/silver-chloride, platinum and platinum-iridium. Typically, any material having requisite bioelectrical properties may be used. The material of electrodes 34A-B, 36A-B may be plated on a substrate which includes desired mechanical properties rather than bioelectrical properties. For example, the electrodes 34A-B, 36A-B may include a Nitinol substrate coated with platinum-iridium.

The electrodes 34A-B, 36A-B may be held peripherally around the inflation balloon 30 at a given longitudinal position using a longitudinal fastening affixed to the distal and proximal portions of the inflation balloon 30. The longitudinal fastening instrument may include, for example, a plurality of non-conductive filaments 40A-D (see FIG. 3A), which may be referred to as tethers or non-conductive tethers. The non-conductive filaments 40A-D may include, for example, a silk, polyester, dacron, and/or polymer blend material such as ETHICON® suture.

Figure 3:
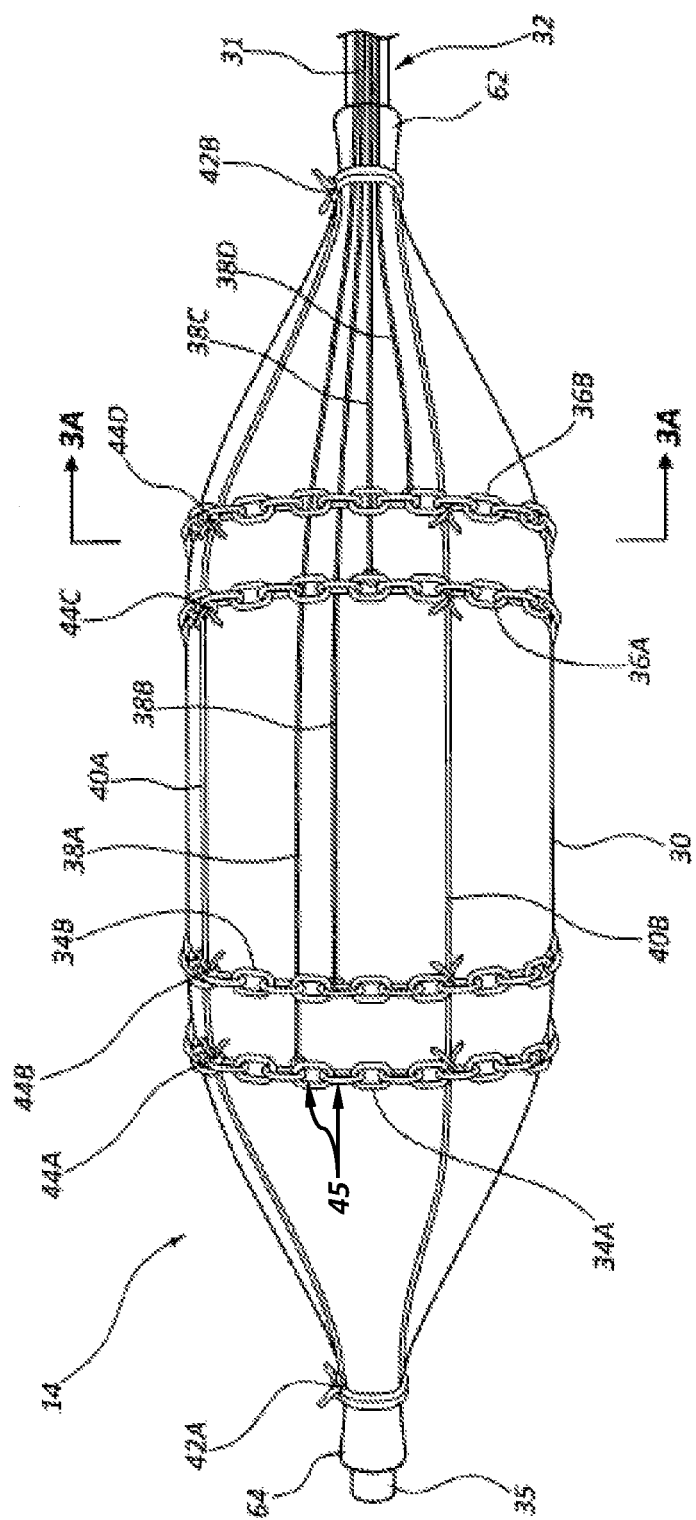
FIG. 3 is a side view of an inflation balloon assembly of the catheter of FIG. 1.
Figure 3A:
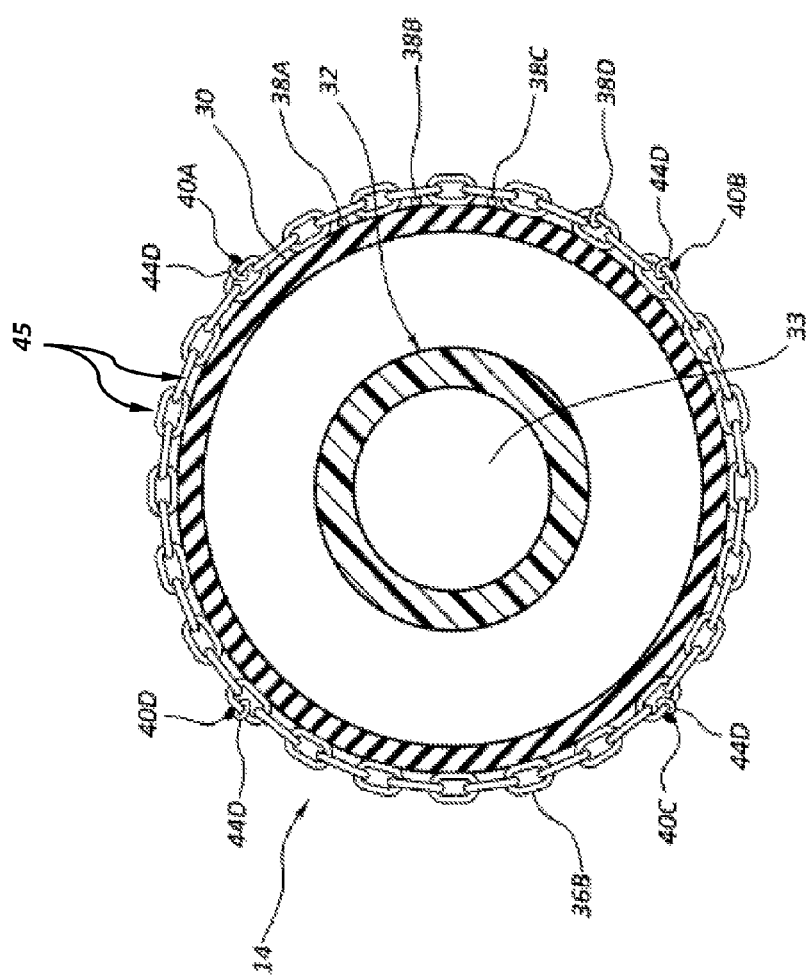
FIG. 3A is a cross-sectional view of the inflation balloon assembly of FIG. 3 taken along cross-section indicators 3A-3A.

The non-conductive filaments 40A-D may be connected to the inflation balloon 30 at proximal and distal waists 62, 64 of the inflation balloon 30 (see FIGS. 1-3 showing non-conductive filaments 40A-B connected to inflation balloon 30). The proximal and distal waists 62, 64 may be connected to the inflation tube 32 at axially spaced apart locations (e.g., at the proximal and distal ends 31, 35). The non-conductive filaments 40A-D may be wrapped around the proximal and distal waists 62, 64 and include distal and proximal filament anchors 42A-B may be used to secure at least some of the non-conductive filaments 40A-D to the inflation balloon 30 (e.g., see non-conductive filament 40A shown in FIG. 3). A portion of the non-conductive filaments 40A-D may be connected to the inflation tube 32 rather than the proximal and distal waists 62, 64 of the inflation balloon 30.

In other examples, the non-conductive filaments 40A-D may be connected at proximal and distal ends thereof to the inflation balloon 30 or to the inflation tube 32 using a bonding agent such as, for example, light cure adhesives (UV light and/or visible light curable adhesives, for example), instant adhesives, acrylics, epoxies, cyanoacrylates, urethane-based adhesives, silicone-based adhesive, and/or surface preparation primers, and the like. The bonding agent may include a pad with at least one of the aforementioned adhesives applied to at least one side of the pad. The pad may secure a portion of the non-conductive filaments 40A-D directly to the inflation tube 32 or to a portion of the inflation balloon 30, such as a portion of the inflation balloon 30 that does not inflate (e.g., the proximal and distal waists 62, 64). In yet another example, the non-conductive filaments 40A-D may be secured using the distal and proximal filament anchors 42A-B and the bonding agent. Many other connection techniques may be used to connect, either releasably or permanently, any one of the non-conductive filaments 40A-D to the inflation balloon 30 or other features of the insertion tube 12 and inflation balloon assembly 14.

The non-conductive filaments 40A-D may connect to at least one link 45 of each electrode (e.g., via electrode anchors 44A-D, as shown in FIG. 3) to maintain an axial position of the electrodes 34A-B, 36A-B relative to the inflation balloon 30. The non-conductive filaments 40A-D may extend between the electrodes 34A-B, 36A-B and an outer surface of the inflation balloon 30. Alternatively, the electrodes 34A-B, 36A-B may extend between the outer surface of the inflation balloon 30 and the non-conductive filaments 40A-D (see FIG. 3A).

The non-conductive filaments 40A-D may maintain an axial position of the electrodes 34A-B, 36A-B orthogonal to the length dimension of the inflation balloon 30. The non-conductive filaments 40A-D may connect to the inflation balloon 30 with a loop formed in the non-conductive filaments 40A-D around the distal and proximal end portions of the inflation balloon 30 (e.g., narrower, smaller diameter portions of the inflation balloon 30). The non-conductive filaments 40A-D may be held in place at least in part by a bonding agent (e.g., held in place by the bonding agent alone; held in place by a loop and the bonding agent; held in place by a loop, a knot, and the bonding agent; etc.).

Any number of non-conductive filaments 40A-D may be used. Using two or more non-conductive filaments 40A-D may provide improved accuracy in maintaining an axial position of the electrodes 34A-B, 36A-B relative to inflation balloon 30.

The non-conductive filaments 40A-D may maintain a physical separation between electrodes 34A-B, 36A-B such that electrodes do not come into contact with each other, which may otherwise create an electrical short between the electrodes 34A-B, 36A-B. Each of the non-conductive filaments 40A-D may attach to the electrodes 34A-B, 36A-B via electrode anchors 44A-D (e.g., see attachment of non-conductive filament 40A to electrodes 34A-B, 36A-B in FIGS. 1-3). In other embodiments, some of the non-conductive filaments 40A-D may connect to only some of the electrodes 34A-B, 36A-B.

The electrode leads 38A-D electrically couple the electrodes 34A-B, 36A-B to controller 16. The electrode leads 38A-D may extend separately to each of the electrodes 34A-B, 36A-B. Alternatively, two or more of the electrode leads 38A-D may be bundled together (e.g., housed within a common wiring sheath or fastened together). In some arrangements, the bundle of electrode leads 38A-D extends between each of the electrodes 34A-B, 36A-B with one of the electrode leads 38A-D terminating at or being electrically connected to one of the electrodes 34A-B, 36A-B. In other embodiments, two or more of the electrodes 34A-B, 36A-B are coupled to a single one of electrode leads 38A-D.

Figure 4:
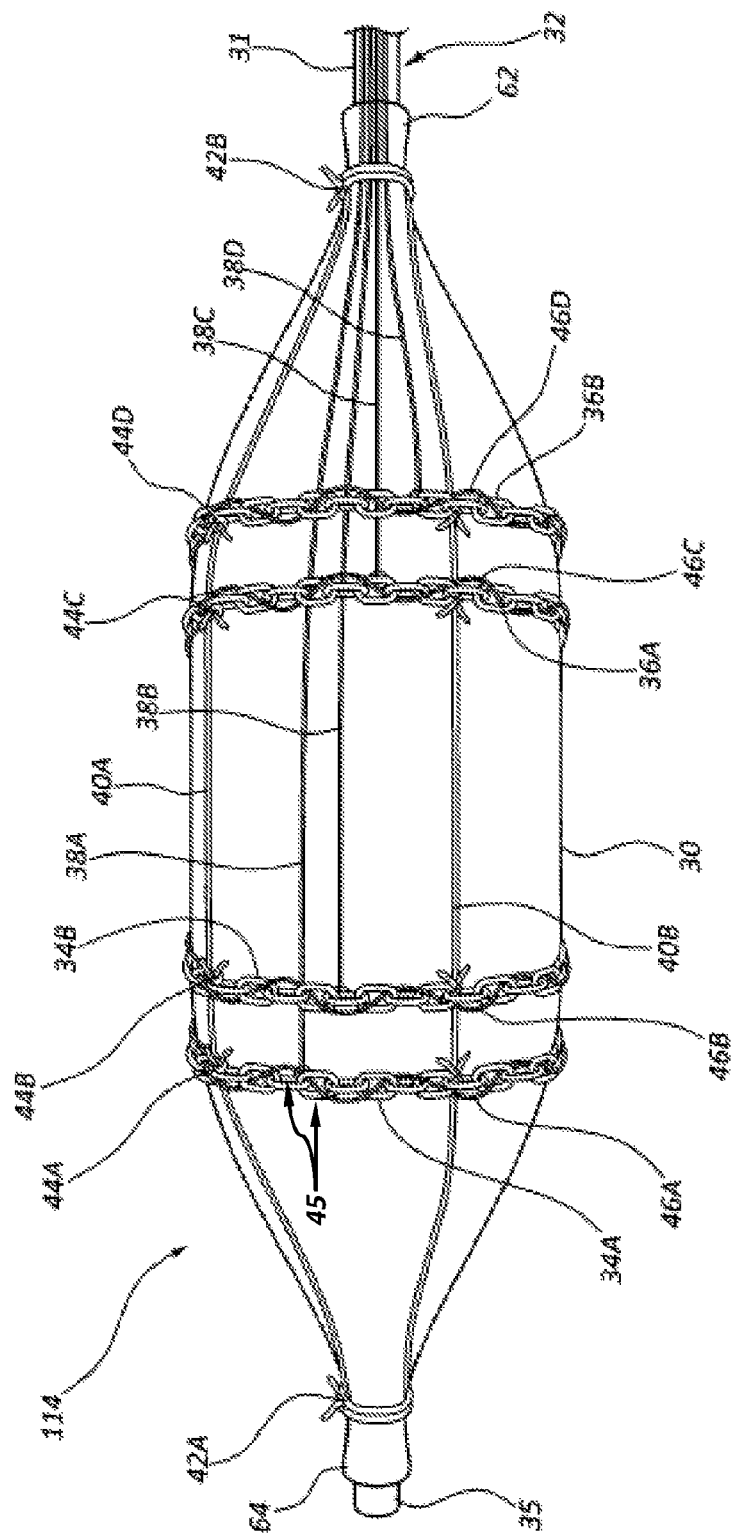
FIG. 4 is a side view of another example inflation balloon assembly for use with the catheter of FIG. 1.

FIG. 4 shows an inflation balloon assembly 114 similar to the inflation balloon assembly 14 of FIGS. 1-3A, the details of which will be repeated briefly. The inflation balloon assembly 114 includes the inflation balloon 30, the inflation tube 32 having proximal and distal ends 31, 35, the electrodes 34A-B, 36A-B, and the electrode leads 38A-D. The axial position of the electrodes 34A-B, 36A-B may be maintained relative to the length of the inflation balloon 30 by a plurality of non-conductive filaments 40A-D, although only non-conductive filaments 40A-B are visible in FIG. 4. The electrodes 34A-B, 36A-B may additionally include conductive filaments 46A-D.

The conductive filaments 46A-D may be threaded through links 45 of the electrodes 34A-B, 36A-B, respectively. The conductive filaments 46A-D may be threaded through at least portions of electrodes 34A-B, 36A-B to limit the possibility of an interruption of conductivity between successive links of the electrodes. The conductive filaments 46A-D may have a continuous loop construction. In other embodiments, the conductive filaments 46A-D may extend along only portions of the lengths of the electrodes 34A-B, 36A-B. The conductive filaments 46A-D may provide improved conductivity along the length of each electrode 34A-B, 36A-B.

Figure 5:
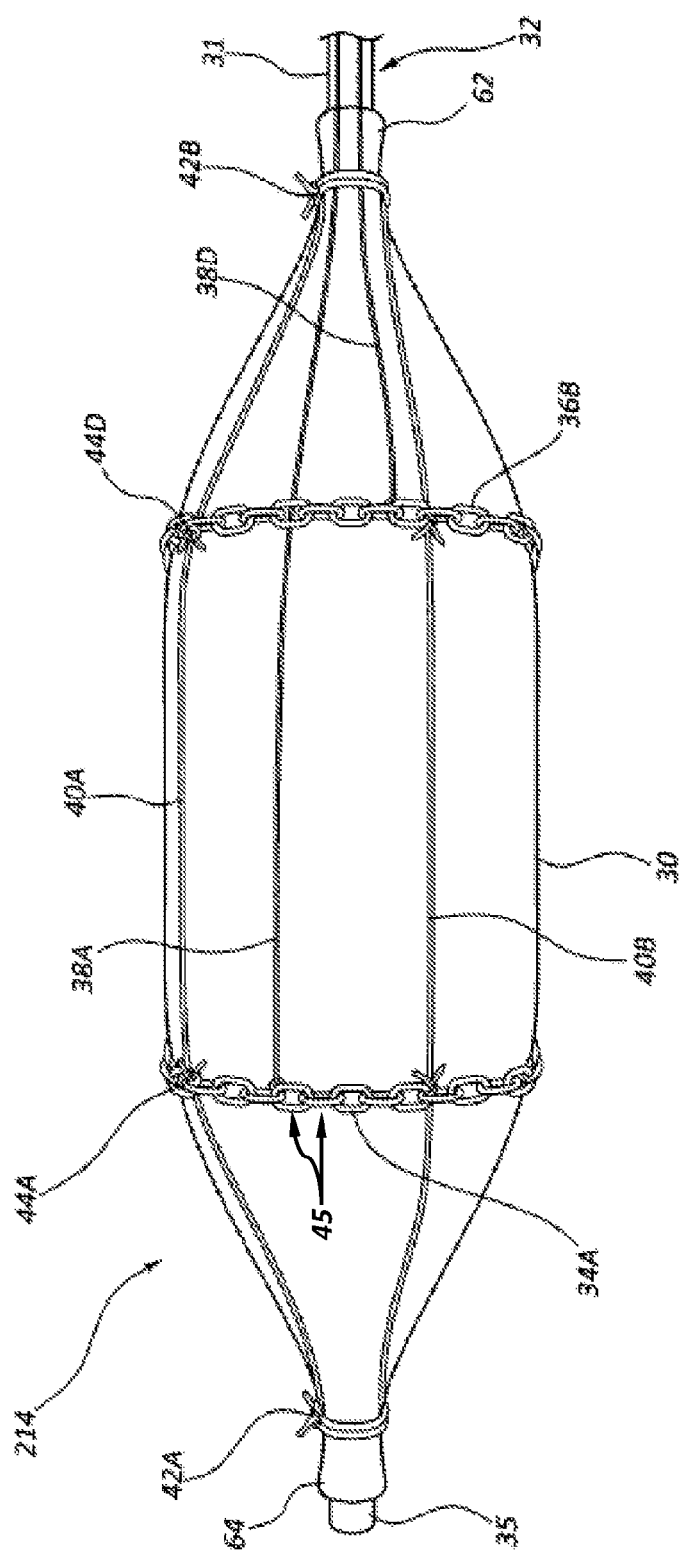
FIG. 5 is a side view of another example inflation balloon assembly for use with the catheter of FIG. 1.

FIG. 5 shows an inflation balloon assembly 214 similar to the inflation balloon assembly 14 of FIGS. 1-3A, the details of which will be repeated briefly. The inflation balloon assembly 214 includes the inflation balloon 30, the inflation tube 32 having proximal and distal ends 31, 35, the electrodes 34A, 36B, and the electrode leads 38A-B. The axial position of the electrodes 34A-B, 36A-B of inflation balloon assembly 214 in FIG. 5 may be maintained along the length of the inflation balloon 30 using non-conductive filaments 40A-D extending along the length of the inflation balloon 30, although only two non-conductive filaments 40A-B are visible.

The inflation balloon assembly 214 may additionally include a single distal electrode 34A and a single proximal electrode 36B rather than multiple distal and proximal electrodes 34A-B, 36A-B as included in the embodiments of FIGS. 1-4. Although depicted with single distal and proximal electrodes 34A, 36B, inflation balloon assembly 214 may include any number or combination of distally positioned electrodes and proximally positioned electrodes. The electrode leads 38A-B may provide conductive connections to electrodes 34A, 36B, respectively. For example, electrode leads 38A-B may supply a conductive connection between controller 16 and electrodes 34A, 36B.

Figure 6:
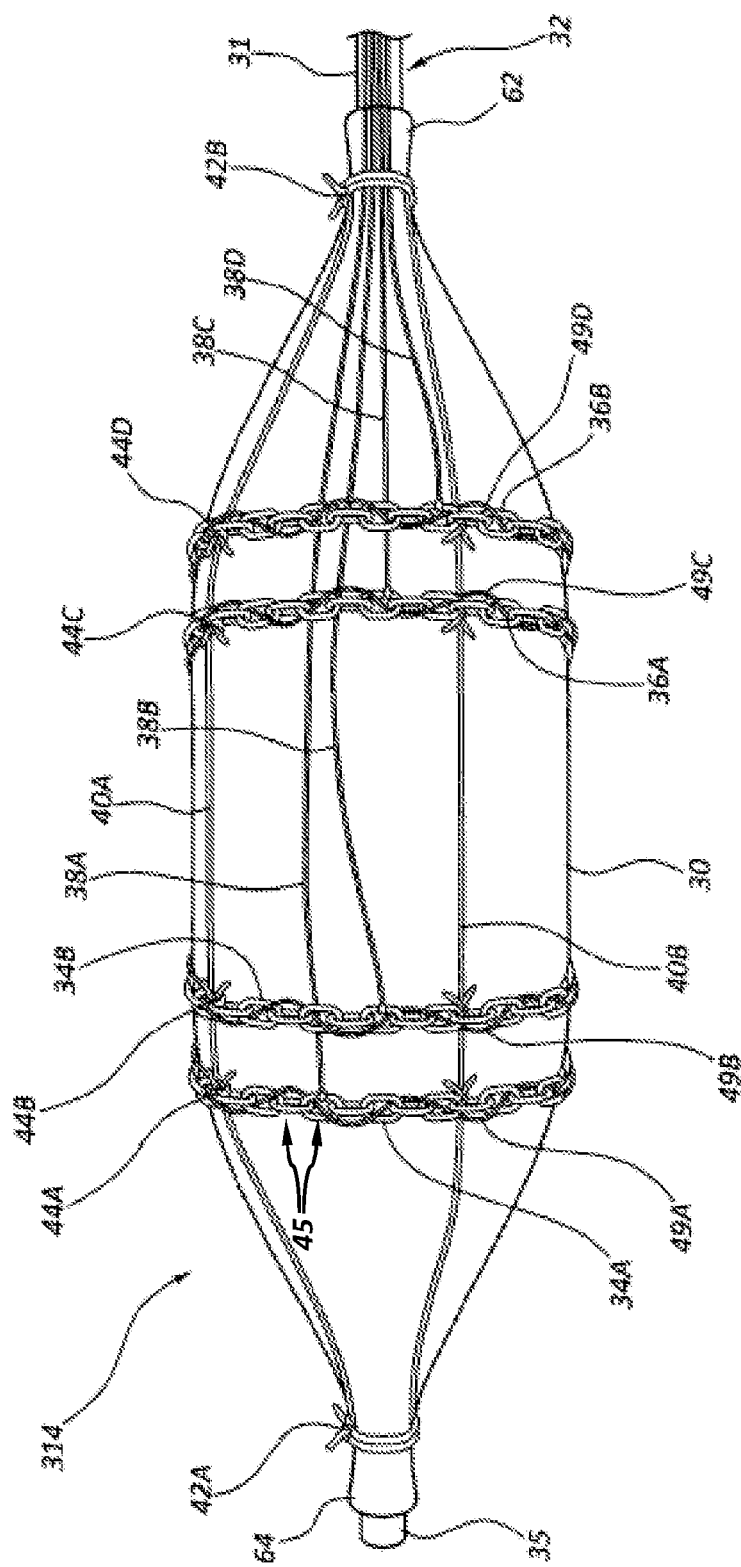
FIG. 6 is a side view of another example inflation balloon assembly for use with the catheter of FIG. 1.

FIG. 6 shows an inflation balloon assembly 314 similar to the inflation balloon assembly 14 of FIGS. 1-3A, the details of which will be repeated briefly. The inflation balloon assembly 314 includes the inflation balloon 30, the inflation tube 32 having proximal and distal ends 31, 35, the electrodes 34A-B, 36A-B, and electrode leads 38A-D. The axial position of the electrodes 34A-B, 36A-B of inflation balloon assembly 314 may be maintained along the length of the inflation balloon 30 by non-conductive filaments 40A-D, although only non-conductive filaments 40A-B are visible in FIG. 6. The electrodes 34A-B, 36A-B may have conductive filaments 46A-D mounted thereto, respectively, to provide improved conductivity along the lengths of the electrodes 34A-B, 36A-B.

Elastic filaments 49A-D may be threaded through one or more of the links 45 of each electrode 34A-B, 36A-B, respectively, to provide a radially inward directed force to electrodes 34A-B, 36A-B. The elastic filaments 49A-D help maintain axial and radial positions of electrodes 34A-B, 36A-B relative to inflation balloon 30 before, during and after balloon deployment. In one configuration, elastic filaments 49A-D include both conductive properties and elastic properties.

Figure 7:
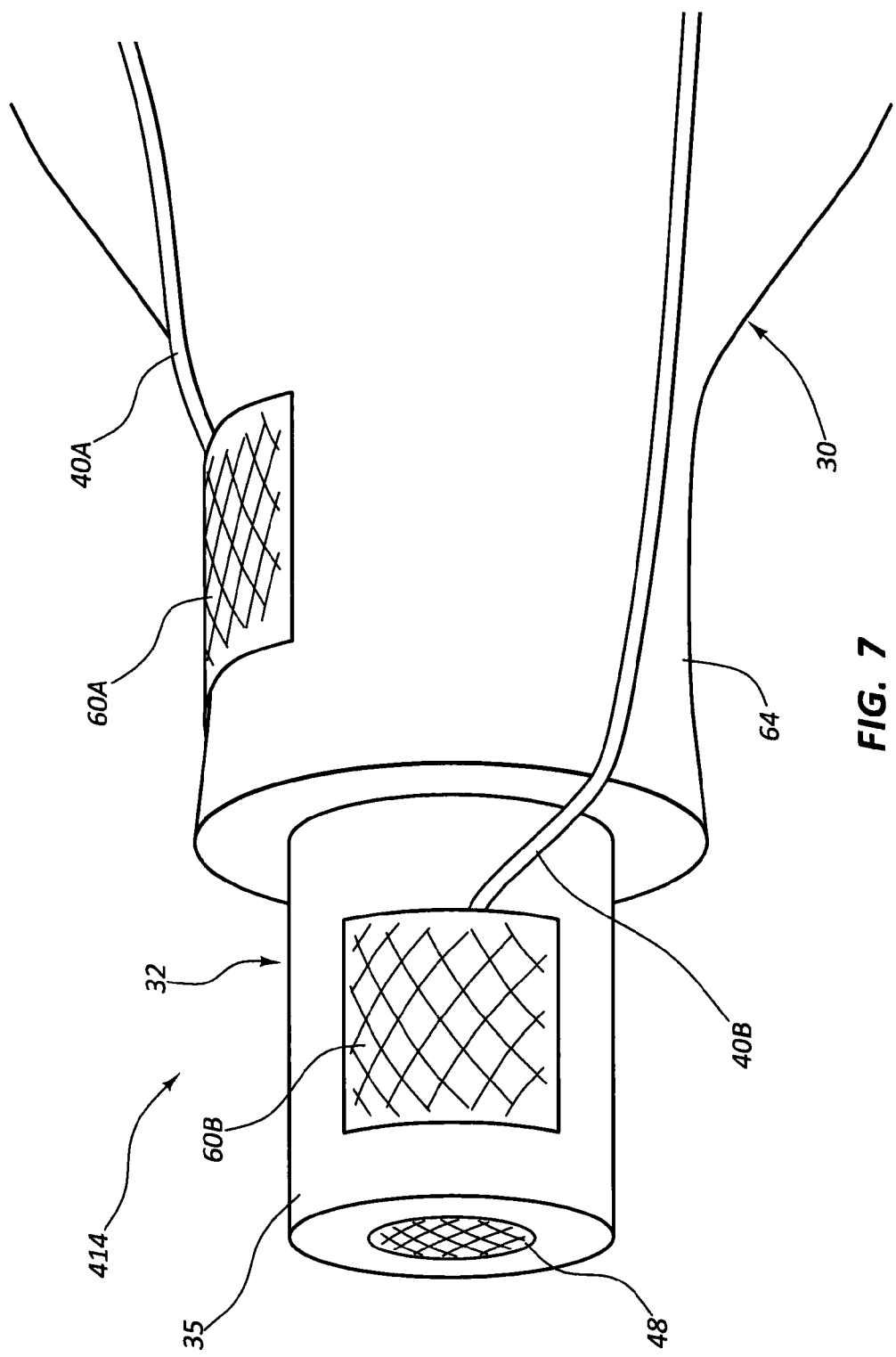
FIG. 7 is a perspective view of a distal end of another example inflation balloon assembly for use with the catheter of FIG. 1.

FIG. 7 shows an inflation balloon assembly 414 similar to the inflation balloon assembly 14 of FIGS. 1-3A, the details of which will be repeated briefly. The inflation balloon assembly 414 includes the inflation balloon 30, the inflation tube 32, an inflation tube plug 48, at least first and second non-conductive filaments 40A-B, and bonding pads 60A-B. The inflation balloon assembly 414 may include electrodes 34A-B, 36A-B (not shown) to which non-conductive filaments 40A-B are secured to maintain axial positions of the electrodes 34A-B, 36A-B relative to inflation balloon 30.

The non-conductive filaments 40A-B of inflation balloon assembly 414 may be affixed to proximal and distal end portions of the inflation balloon 30. For example, the non-conductive filament 40A may be affixed to the distal waist 64 of the inflation balloon 30. The non-conductive filament 40B may be affixed to the distal end 35 of the inflation tube 32. The non-conductive filaments 40A-B may be affixed to the inflation balloon 30 or inflation tube 32 using a bonding agent via, for example, bonding pads 60A-B shown in FIG. 7. Bonding pads 60A-B may include a pad with an adhesive applied to at least one side of the pad. Alternatively, a volume of adhesive may be applied directly to the outer surface of the inflation balloon 30 or inflation tube 32 to secure the non-conductive filament 40A-B in place. Any additional non-conductive filaments used to maintain axial positions of the electrodes 34A-B, 36A-B may bonded directly to inflation balloon 30 and inflation tube 32.

Figure 8:
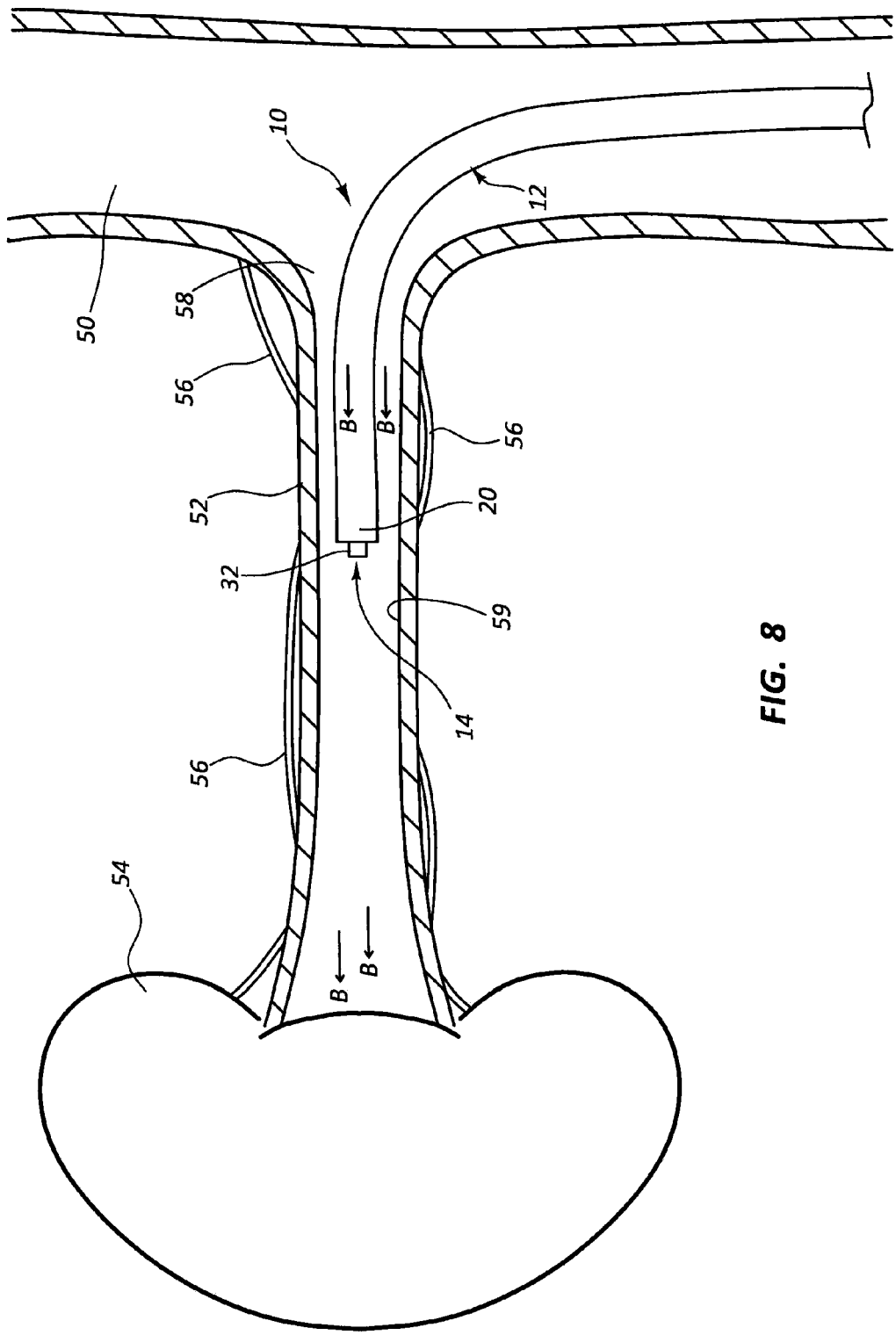
FIG. 8 shows the catheter of FIG. 1 positioned in a renal artery.
Figure 9:
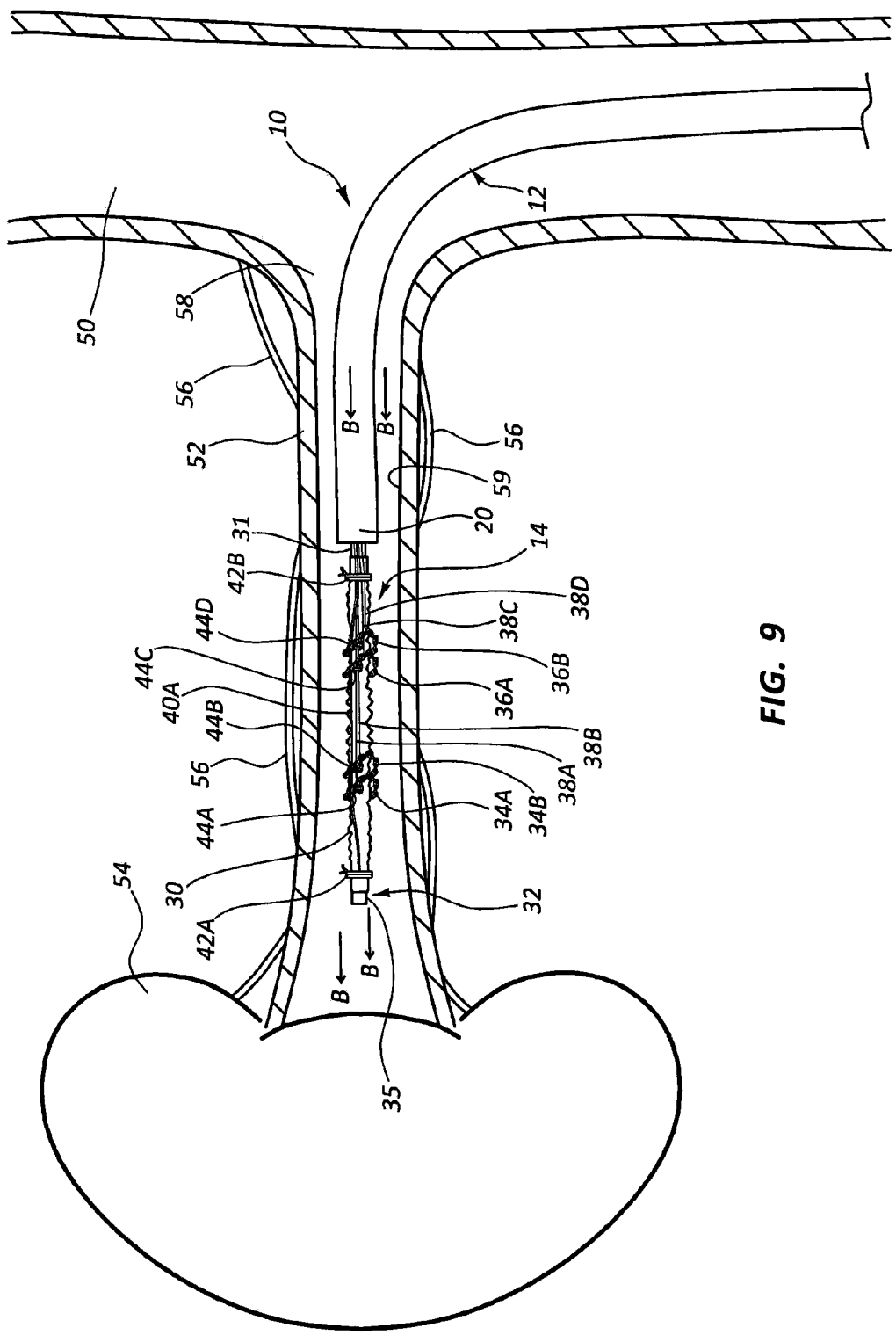
FIG. 9 shows the catheter of FIG. 8 with the inflation balloon assembly deployed from a carrier tube and in the deflated position.
Figure 10:
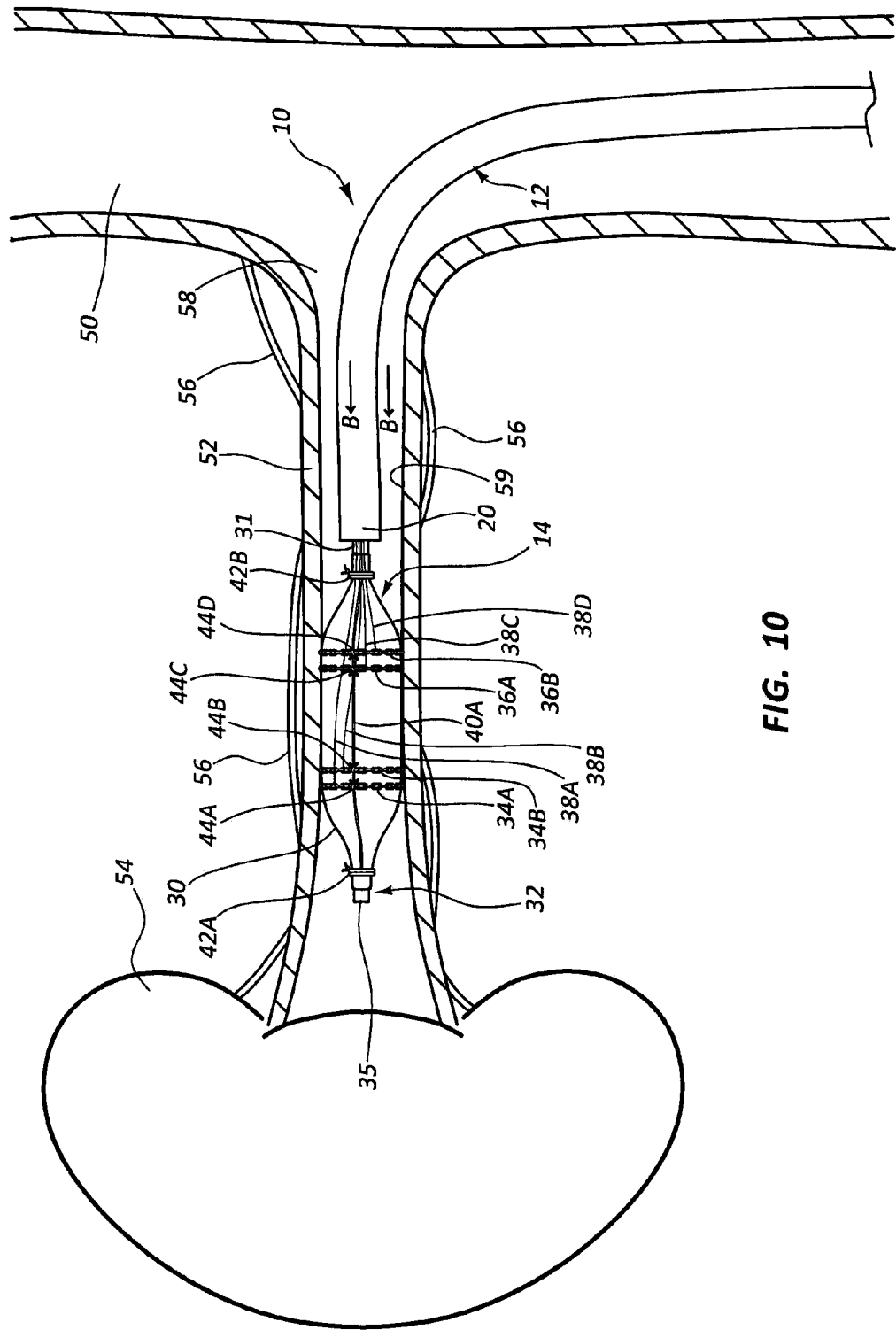
FIG. 10 shows the catheter of FIG. 9 with the inflation balloon assembly in the inflated position to arrange an electrode in contact with an inner surface of the renal artery.

Referring now to FIGS. 8-10, the catheter 10 of FIGS. 1-2 is shown in use in a renal artery 52. The catheter 10 is inserted through an aorta 50 and into the renal artery 52. The renal artery 52 provides blood flow to kidney 54. A plurality of renal nerves 56 may extend along an exterior of the renal artery 52 and may be positioned in a side wall of the renal artery 52. The renal artery 52 may have an ostium 58 leading from the aorta 50 and an inner surface 59.

FIG. 8 shows the inflation balloon assembly 14 in a retracted position, wherein at least a portion of the inflation balloon assembly 14 is located within the inner lumen of the insertion tube 12. FIG. 9 shows the inflation balloon assembly 14 advanced beyond the distal end 20 of the insertion tube 12, with the inflation balloon 30 in a deflated, unexpanded state. The inflation balloon 30 may be advanced until at least the proximal end of the inflation balloon 30 extends beyond the distal end 20 of the insertion tube 12. With the inflation balloon assembly 14 deployed from the insertion tube 12, the inflation balloon 30 may then be inflated, as shown in FIG. 10.

The inflation balloon 30 is inflated until the electrodes 34A-B, 36A-B are positioned in contact with the inner surface 59 of the renal artery 52. At least one of the electrodes 36A-B may be operated (e.g., via controller 16) to stimulate physiologic activity in renal artery 52, such as stimulating the renal artery 52 and/or at least one of the renal nerves 56. At least one of the electrodes 34A-B is operated (e.g., via controller 16) to sense activity in renal artery 52 and/or at least one of the renal nerves 56 in response to the stimulations generated by at least one of electrodes 36A-B. The data collected by the electrodes 34A-B may be recorded (e.g., via controller 16) as a baseline of activity prior to ablating.

At least one of the electrodes 34A-B, 36A-B may be operated (e.g., via controller 16) to ablate the renal artery 52 and/or renal nerves 56. In some arrangements, any one of the electrodes 34A-B, 36A-B may be operable (e.g., via controller 16) to ablate. At least some of the electrodes 34A-B, 36A-B may be configured to ablate and at least one of stimulate and sense. Ablating may be done by supplying energy (e.g., RF energy) to at least one of the electrodes 34A-B, 36A-B, which generates heat and eventually kills or otherwise permanently damages renal artery 52 and/or at least some of the renal nerves 56. Providing the electrodes 34A-B, 36A-B as circumferential electrodes may improve the chance of ablating at least some of the renal nerves 56 as compared to using electrodes having less than a full circumferential contact with the inner surface 59 of the renal artery 52.

After ablating using at least one of the electrodes 34A-B, 36A-B, at least one of the electrodes 36A-B may again be operated to stimulate the renal artery 52 and/or at least one of the renal nerves 56. At least one of the electrodes 34A-B may be operated to sense activity in the renal artery 52 and/or the at least one renal nerve 56. The amount of activity sensed by the at least one electrode 34A-B may be compared to the activity detected prior to the ablation. A change (e.g., reduction) in the detected activity may indicate the efficacy of the ablation.

In some embodiments, the inflation balloon 30 may be at least partially deflated in order to reposition the inflation balloon assembly 14 into another axial location in the renal artery 52. With the inflation balloon assembly 14 repositioned, the inflation balloon 30 may be re-inflated in order to provide contact between the electrodes 34A-B, 36A-B and the inner surface 59 of the renal artery 52. Further stimulation and sensing of activity in the renal artery 52 and/or the renal nerves 56 may be performed after repositioning the inflation balloon assembly 14 using at least one of the electrodes 34A-B, 36A-B. Additional ablating of the renal artery 52 and renal nerves 56 using at least some of the electrodes 34A-B, 36A-B may be performed as needed after repositioning the inflation balloon assembly 14.

Inflating the inflation balloon 30 may stop blood flow B through the renal artery 52 in the area of the electrodes 34A-B, 36A-B. Limiting the blood flow B may help electrically isolate the electrodes 34A-B, 36A-B, which may provide at least one of improved electrical stimulation of the renal nerves 56 and sensing of electrical activity in the renal nerves 56. The blood flow B, if permitted to contact the electrodes 34A-B, 36A-B during operation, may create additional signal noise, which may limit the accuracy of electrical measurements using the electrodes 34A-B, 36A-B.

Figure 11:
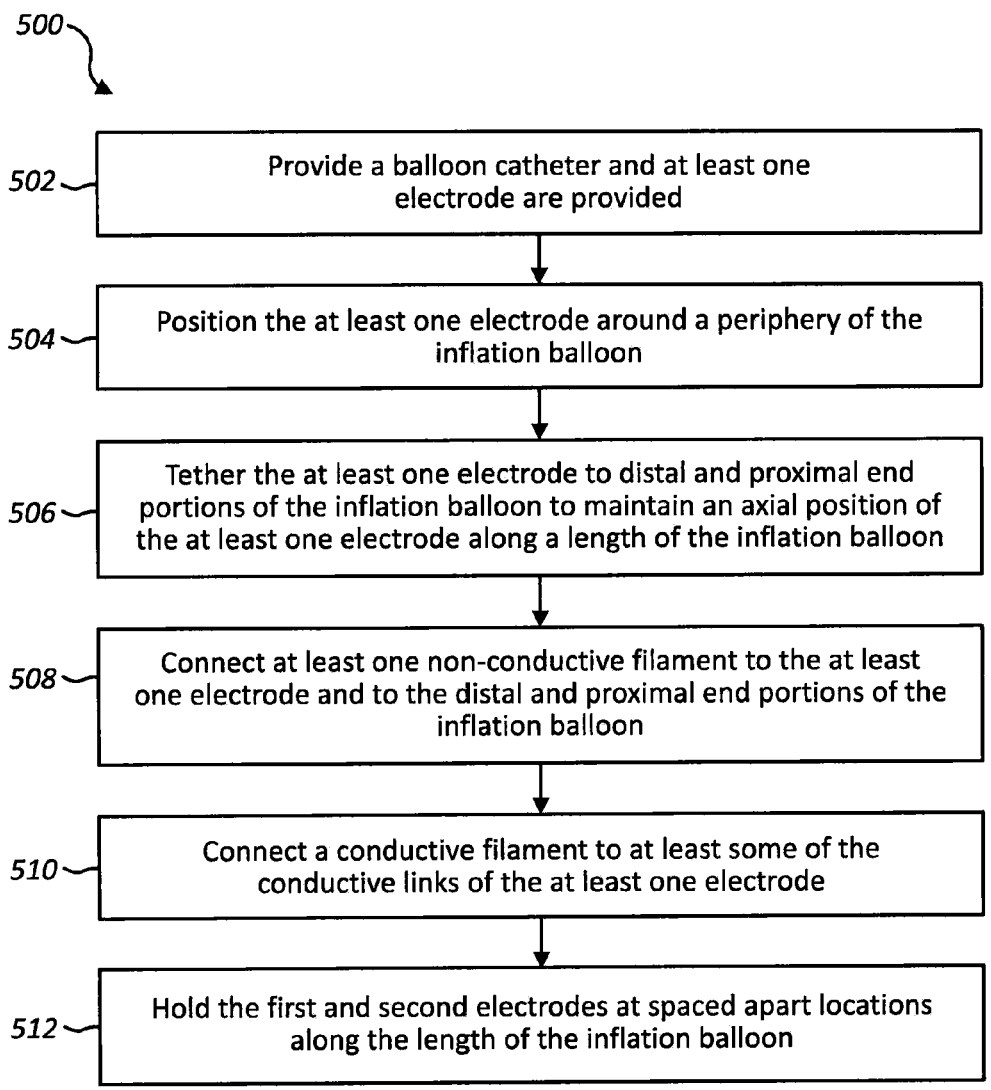
FIG. 11 is a flowchart showing steps of a method for assembling an ablation catheter.

Referring to FIG. 11, a flowchart of a method 500 for assembling an ablation catheter is depicted. For clarity, the method 500 is described below with reference to the inflation balloon assemblies disclosed herein.

At block 502, a balloon catheter and at least one electrode are provided. The balloon catheter may include an inflation balloon. The at least one electrode may include a plurality of conductive links coupled together. The at least one electrode may have a loop construction and may be expandable from a collapsed position to an expanded position. At block 504, the at least one electrode may be positioned around a periphery of the inflation balloon. At block 506, the at least one electrode may be tethered to distal and proximal end portions of the inflation balloon to maintain an axial position of the at least one electrode along a length of the inflation balloon. At block 508, at least one non-conductive filament may be connected to the at least one electrode and to the distal and proximal end portions of the inflation balloon.

At block 510, at least one conductive filament may be connected to at least some of the conductive links of the at least one electrode. In one embodiment, the at least one electrode may include at least first and second electrodes. At 512, the first and second electrodes may be held at spaced apart locations along the length of the inflation balloon.

Therefore, the method 500 may provide assembly of an ablation catheter. It should be noted that the method 500 is just one implementation and that the operations of the method 500 may be rearranged or otherwise modified such that other implementations are possible.

As used in this specification and the appended claims, the terms "engage" and "engagable" are used broadly to mean interlock, mesh, or contact between two structures or devices. A "tube" is an elongated device with a passageway. A "lumen" refers to any open space or cavity in a bodily organ, especially in a blood vessel. The words "including" and "having," as well as their derivatives, as used in the specification, including the claims, have the same meaning as the word "comprising."

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A catheter, comprising:
an inflation balloon inflatable within a vessel; and
at least one chain electrode extending around at least a portion of a periphery of the inflation balloon, the at least one chain electrode comprising a circumferential ring formed from a plurality of individual closed rings linked around the periphery of the inflation balloon, wherein each individual closed ring comprises no more than two linking points, the at least one chain electrode being expandable as the inflation balloon is inflated and contractible as the inflation balloon is deflated, the at least one chain electrode maintaining an axial position orthogonal to a length dimension of the inflation balloon, and the at least one chain electrode being configured to provide at least one of ablation, electrical stimulation, or electrical sensing.

2. The catheter of claim 1, further comprising a non-conductive filament connected to the inflation balloon and to the at least one chain electrode to maintain the position of the at least one chain electrode relative to the inflation balloon.

3. The catheter of claim 2, wherein the non-conductive filament is connected to distal and proximal ends of the inflation balloon.

4. The catheter of claim 3, wherein the non-conductive filament is connected to the distal and proximal ends of the inflation balloon with one of a loop formed in the non-conductive filament or a bonding agent.

5. The catheter of claim 1, wherein the at least one chain electrode includes first and second chain electrodes positioned at spaced apart locations along a length of the inflation balloon.

6. The catheter of claim 5, wherein the first chain electrode is configured to electrically stimulate at least one nerve, and the second chain electrode is configured to detect an electrical activity in the at least one nerve.

7. The catheter of claim 1, further comprising an elastic member coupled to the at least one chain electrode, the elastic member providing a radially inward force to the at least one electrode.

8. The catheter of claim 1, wherein the plurality of individual closed rings linked around the periphery of the inflation balloon includes a plurality of linked conductive rings.

9. The catheter of claim 8, further comprising at least one conductive filament coupled to at least some of the plurality of individual closed rings.

10. The catheter of claim 1, wherein the inflation balloon is operable within the vessel between a deflated position and an inflated position, the inflation balloon configured such that the inflation balloon in the inflated position temporarily blocks blood flow through the vessel and positions the at least one chain electrode in contact with an inner surface of the vessel.

11. The catheter of claim 1, wherein the plurality of individual closed rings linked around the periphery of the inflation balloon includes a plurality of linked conductive and non-conductive rings.

12. The catheter of claim 1, wherein the at least one chain electrode comprises a plurality of conductive filaments.

* * * * *